(12) United States Patent
Watanabe et al.

(10) Patent No.: US 6,509,390 B2
(45) Date of Patent: Jan. 21, 2003

(54) TWO-PASTE DENTAL ALGINATE IMPRESSION MATERIAL

(75) Inventors: Nobutaka Watanabe, Tokyo (JP); Hiroshi Kamohara, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/946,332

(22) Filed: Sep. 6, 2001

(65) Prior Publication Data

US 2002/0058725 A1 May 16, 2002

(30) Foreign Application Priority Data

Sep. 8, 2000 (JP) ........................................ 2000-273594

(51) Int. Cl.$^7$ ............................ A61K 6/10; A61K 6/097; C08L 5/00; C08L 3/10; C08L 3/30
(52) U.S. Cl. ...................... 523/109; 523/115; 523/116; 523/118; 523/120; 524/28; 524/55; 524/423; 524/425; 524/448
(58) Field of Search .................................. 523/115, 116, 523/118, 109, 120; 524/448, 28, 55, 423, 425

(56) References Cited

U.S. PATENT DOCUMENTS 4,626,558 A * 12/1986 Pellico .......................... 523/109
5,900,230 A * 5/1999 Cutler ............................ 424/49

* cited by examiner

*Primary Examiner*—Tae H. Yoon
(74) *Attorney, Agent, or Firm*—Oblon, Spivak, McClelland, Maier & Neustadt, P.C.

(57) ABSTRACT

The dental alginate impression material comprising a main paste containing an alginate, water and a filler as major components and a setting paste containing calcium sulfate and a liquid component as major components, the both pastes being to be mixed and set, wherein the main paste further contains 0.01 to 15% by weight of one or two or more polysaccharides selected from the group consisting of carrageenan, pullulane, curdlan, xanthane gum, gellan gum, pectin, konjak glucomannan, xyloglucan, guar gum, gum arabic, and locust bean gum, and the setting paste further contains 0.5 to 50% by weight of polybutene, is provided to thereby make the composition superior in preservability, and free from change of viscosity of the main paste with time, from liquid separation and deterioration of the setting paste, and from a delay in setting time due to the preservation.

15 Claims, No Drawings

TWO-PASTE DENTAL ALGINATE IMPRESSION MATERIAL

BACKGROUND OF THE INVENTION

1. Field of the Invention

The present invention relates to a dental alginate impression material to be used for taking an impression in the oral cavity in the dentistry, which is set upon mixing two types of pastes, i.e., a main paste and a setting paste. In particular, the present invention relates to a dental alginate impression material that is superior in preservability, is free from change of viscosity of the main paste with time and from liquid separation of the setting paste, and does not cause a delay in setting time during the preservation.

2. Description of the Conventional Art

In the dentistry, as an impression material for taking an impression in the oral cavity during the preparation of a prosthesis, is widely used a dental alginate impression material. The dental alginate impression material includes one which is usually provided in the form of a powder containing an alginate, a gelling reaction material, a gelling adjustment material, and a filler as major components and is set by mixing with water during the use; and one which is provided in the form of two types of pastes, i.e., a main paste and a setting paste, and is set by mixing these pastes during the use. And, in recent years, for the reasons that the mixing is easy and that it is possible to achieve automatic mixing, and so on, a pasty alginate impression material comprising a main paste and a setting paste is frequently used.

In this pasty alginate impression material, usually, the main paste is constructed of a paste prepared by dissolving an alginate in water and adding a filler as a component for imparting shaping properties and hardness to the solution; and the setting paste is constructed of a paste comprising a mixture of calcium sulfate, as setting materials for the alginate, and a liquid substance such as liquid paraffin. These pasty alginate impression materials are easy for mixing, and can be continuously mixed and extruded by using an exclusive instrument. Accordingly, they are very convenient for dentists or hygienists and are frequently used.

However, the currently used pasty alginate impression material are poor in preservability. Further, the main paste thereof is remarkable in change of the viscosity with time, and the setting paste thereof is liable to cause separation between calcium sulfate and the liquid component. As a result, when the main paste is mixed with the setting paste, the mixture is liable to become poor, whereby inconvenience arises such that an accurate impression cannot be obtained. In addition, in the case where the viscosity changes, the fluidity of the mixed material also changes. As a result, there are inconveniences such that a minute impression cannot be taken or that dropping of the paste occurs in the depth of the throat. Moreover, the setting paste is remarkable in deterioration with time, and the setting time is delayed. As a result, it is not set within a usual holding time in the mouth, leading to causing an incomplete impression.

SUMMARY OF THE INVENTION

The present invention is aimed at developing a pasty dental alginate impression material comprising a main paste and a setting paste, which is superior in preservability, is free from change of viscosity of the main paste with time and from liquid separation and deterioration of the setting paste, and has no possibility to cause a delay in setting time during the preservation.

In order to achieve the above-described aim, we, the present inventors made extensive and intensive investigations. As a result, it has been found that, when one or two or more polysaccharides selected from the group consisting of carrageenan, pullulane, curdlan, xanthane gum, gellan gum, pectin, konjak glucomannan, xyloglucan, guar gum, gum arabic, and locust bean gum are added to the conventional main paste containing an alginate, water and a filler as major components, the change of viscosity with time is suppressed, while when polybutene is added to a setting paste containing calcium sulfate and a liquid component as major components, the liquid separation and deterioration are suppressed, leading to the accomplishment of the present invention.

Specifically, the present invention is concerned with a dental alginate impression material comprising two types of pastes of a main paste containing an alginate, water and a filler as major components and a setting paste containing calcium sulfate and a liquid component as major components, the both pastes being to be mixed and set, wherein the main paste further contains 0.01 to 15% by weight of one or two or more polysaccharides selected from the group consisting of carrageenan, pullulane, curdlan, xanthane gum, gellan gum, pectin, konjak glucomannan, xyloglucan, guar gum, gum arabic, and locust bean gum, and the setting paste further contains from 0.5 to 50% by weight of polybutene.

DESCRIPTION OF THE PREFERRED EMBODIMENTS

Of the alginate, water and filler used as the major components of the main paste according to the present invention, is used, as the alginate, at least one water-soluble salt such as sodium, potassium, ammonium and triethanolamine salts of alginic acid. The alginate is usually contained in an amount of from about 1 to 10% by weight in the main paste. As the water, any of ion exchanged water and distilled water may be used. Also, water subjected to sterilization treatment with sodium hypochlorite, etc. may be used. As the filler, is used at least one powder such as diatomaceous earth, silicicanhydride, talc, calcium carbonate, and perlite.

Of the calcium sulfate and liquid component used as the major components of the setting paste, is used a dihydrate or hemihydrate of clacium sulfate, as the calcium sulfate. As the liquid component, are used liquid paraffin, aliphatic alcohols, and fatty acids.

In the case where the composition is composed only of these components used for the usual pasty dental alginate impression material, the viscosity of the main paste changes with time as described above. Accordingly, in the present invention, one or two or more polysaccharides selected from the group consisting of carrageenan, pullulane, curdlan, xanthane gum, gellan gum, pectin, konjak glucomannan, xyloglucan, guar gum, gum arabic, and locust bean gum are added as a component for preventing the change of viscosity of the main paste with time. These polysaccharides are stable in the alginate aqueous solution and are hardly decomposed. Therefore, reduction of the viscosity of the paste hardly occurs.

Of these polysaccharides, carrageenan is one of seaweed polysaccharides and is an acidic polymer comprising galactose containing a sulfate group and an anhydro group. Pullulane, curdlan, xanthane gum, and gellan gum are obtained by separating and purifying polysaccharides produced by microorganisms such as yeast. Of these, is the most useful xanthane gum, which is a viscous polysaccharide produced by bacteria separated from a cabbage leaf surface. Pectin, konjakglucomannan, xyloglucan, guar gum, gum arabic, and locust bean gum are polysaccharides extracted from barks, seeds, leaf stems, subterranean stems, fruits, and the like of plants. Such one or two or more polysaccharides selected from the group consisting of carrageenan, pullulane, curdlan, xanthane gum, gellan gum, pectin, konjak glucomannan, xyloglucan, guar gum, gum arabic, and locust bean gum may be contained in an amount of 0.01 to 15% by weight in the main paste containing an alginate, water and a filler as major components. When the content of the polysaccharide(s) is less than 0.01% by weight, the effect for suppressing the change of viscosity of the main paste with time is insufficient. On the other hand, when it exceeds 15% by weight, the viscosity is too high so that the mixing becomes difficult, resulting in hindrance of the impression taking operation. Preferably, the content of the polysaccharide(s) is 0.1 to 3% by weight.

With respect to the setting paste, the currently used setting paste as described above, which contains calcium sulfate and a liquid component such as liquid paraffin, aliphatic alcohols, and fatty acids as major components, causes the separation of calcium sulfate, so that it is difficult to keep the setting paste as a homogenous paste. Thus, in the present invention, it is designed to prevent the separation of calcium sulfate from the liquid component by adding polybutene thereto.

This polybutene is a liquid polymer composed mainly of isobutylene and having a little amount of 1-butene copolymerized therewith. Usually, those having a number average molecular weight of 300 to 4,000 are used. When this polybutene is added to the setting paste, not only the viscosity of the liquid component increases, but also calcium sulfate is uniformly dispersed and stabilized in the liquid component, whereby the separation of calcium sulfate from the liquid component hardly occurs. Further, since calcium sulfate is uniformly dispersed in the setting paste, it is possible to prevent the calcium sulfate from change of properties during the preservation and the setting time from a delay. The polybutene may be contained in an amount of 0.5 to 50% by weight in the setting paste. When the content of the polybutene is less than 0.5% by weight, the calcium sulfate is separated from the liquid component. On the other hand, when it exceeds 50% by weight, not only the setting time becomes longer, but also the strength of the set material is lowered.

In addition, so far as the characteristics of the dental alginate impression material according to the present invention are not lost, the main paste may further contain various inorganic or organic coloring agents, antiseptics, various disinfectants, flavors or perfumes, and the like; and the setting paste may further contain retarders, pH regulators such as magnesium oxide or hydroxide, surfactants for improving the mixing properties with the main paste, fluorides for improving the model surface, and the like.

Next, the present invention will be described in detail with reference to the following Examples, but it should not be construed that the present invention is limited thereto.

EXAMPLE 1

Main Paste

Sodium alginate: 5% by weight

Diatomaceous earth: 8% by weight

Distilled water: 75% by weight

Locust bean gum: 12% by weight

Setting Paste

Calcium sulfate hemihydrate: 50% by weight

Liquid paraffin: 49.5% by weight

Polybutene (a number average molecular weight: 2,900): 0.5% by weight

The above-described components were well mixed in a mixer to prepare a dental alginate impression material comprising the main paste and the setting paste.

Next, the viscosity of the main paste was measured by means of a B type viscometer. Further, in order to measure the change of viscosity with time, the main paste was filled in an aluminum-made packaging material, and after having been left at 60 ° C. for one week, the viscosity of the resulting main paste was again measured in the same manner. With respect to the liquid separation of the setting paste, 20 ml of the setting paste was measured in a test tube, which was then plugged. After having been left at 60 ° C. for one week, the height of the separated liquid component was measured. Further, in order to examine the change of setting time with time, first of all, the main paste and the setting paste were mixed in a volume ratio of 5:1, and the setting time was measured according to JIS T6505. Thereafter, the main paste and the setting paste were each filled in an aluminum-made packaging material. After having been left at 60 ° C. for one week, the two pastes were again mixed in a volume ratio of 5:1 in the same manner, and the setting time was measured according to JIS T6505, thereby examining the change of setting time with time. The results obtained are summarized and shown in Table 1.

EXAMPLE 2

Main Paste

Sodium alginate: 10% by weight

Diatomaceous earth: 16% by weight

Distilled water: 73.99% by weight

Glucomannan: 0.01% by weight

Setting Paste

Calcium sulfate hemihydrate: 40% by weight

Liquid paraffin: 5% by weight

Polybutene (a number average molecular weight: 390): 55% by weight

The above-described components were well mixed in a mixer to prepare a dental alginate impression material comprising the main paste and the setting paste. Next, the same tests as in Example 1 were carried out. The results obtained are summarized and shown in Table 1.

EXAMPLE 3

Main Paste

Sodium alginate: 7% by weight

Diatomaceous earth: 20% by weight

Distilled water: 72% by weight

Xanthane gum: 1% by weight

Setting Paste

Calcium sulfate hemihydrate: 50% by weight

Liquid paraffin: 48% by weight

Polybutene (a number average molecular weight: 1,400): 2% by weight

The above-described components were well mixed in a mixer to prepare a dental alginate impression material comprising the main paste and the setting paste. Next, the same tests as in Example 1 were carried out. The results obtained are summarized and shown in Table 1.

EXAMPLE 4

Main Paste
- Sodium alginate: 7% by weight
- Diatomaceous earth: 20% by weight
- Distilled water: 71.89% by weight
- Xanthane gum: 1% by weight
- Ethyl p-hydroxybenzoate: 0.1% by weight
- Sodium hypochlorite: 0.01% by weight Polybutene (a number average molecular weight: 1,400): 0.1% by weight The above-described components were well mixed in a mixer to prepare a dental alginate impression material comprising the main paste and the setting paste. Next, the same tests as in Example 1 were carried out. The results obtained are summarized and shown in Table 1.

TABLE 1

|  |  | Example No. | | | | Comparative Example No. | |
|---|---|---|---|---|---|---|---|
|  |  | 1 | 2 | 3 | 4 | 1 | 2 |
| Viscosity of main paste (cps) | Just after the preparation | 45000 | 42700 | 44200 | 44500 | 44100 | 44800 |
|  | After 60° C. for one week | 44500 | 42100 | 44050 | 44200 | 32100 | 44650 |
| Liquid separation of setting paste (mm) |  | No liquid separation | No liquid separation | No liquid separation | No liquid separation | 4 | 4 |
| Change of setting time (sec.) |  | No change occurred. | No change occurred. | No change occurred. | No change occurred. | One minute delayed. | One minute delayed. |

Setting Paste
- Calcium sulfate hemihydrate: 50% by weight
- Liquid paraffin: 36% by weight
- Polybutene (a number average molecular weight: 1,400): 2% by weight
- Potassium fluorotitanate: 5% by weight
- Magnesium hydroxide: 5% by weight
- Polyoxyethylene nonyl phenyl ether 2% by weight The above-described components were well mixed in a mixer to prepare a dental alginate impression material comprising the main paste and the setting paste. Next, the same tests as in Example 1 were carried out. The results obtained are summarized and shown in Table 1.

COMPARATIVE EXAMPLE 1

Main paste
- Sodium alginate: 8% by weight
- Diatomaceous earth: 20% by weight
- Distilled water: 72% by weight Setting paste
- Calcium sulfate hemihydrate: 50% by weight
- Liquid paraffin: 50% by weight The above-described components were well mixed in a mixer to prepare a dental alginate impression material comprising the main paste and the setting paste. Next, the same tests as in Example 1 were carried out. The results obtained are summarized and shown in Table 1.

COMPARATIVE EXAMPLE 2

Main paste
- Sodium alginate: 7% by weight
- Diatomaceous earth: 20% by weight
- Distilled water: 71% by weight
- Xanthane gum: 2% by weight Setting paste
- Calcium sulfate hemihydrate: 50% by weight
- Liquid paraffin: 49.9% by weight As is clear from Table 1, the viscosity of the main pastes in the Examples according to the present invention did not greatly change even after lapsing of one week at 60° C., as compared with that just after the preparation. Further, with respect to the setting pastes in the Examples according to the present invention, no liquid separation occurred even after lapsing of one week at 60° C. Similarly, even when, after lapsing of one week at 60° C., the main paste and the setting paste were mixed with each other, no change of the setting time was found. However, in Comparative Example 1 where the main paste did not contain a polysaccharide, and the setting paste did not contain polybutene, the viscosity of the main paste was lowered, the liquid separation of the setting paste occurred, and a delay of the setting time occurred. Further, in Comparative Example 2 where the setting paste did not contain polybutene, while the main paste contained a polysaccharide, the viscosity of the main paste did not change, but the liquid separation and a delay of the setting time were observed in the setting paste.

In the light of the above, the dental alginate impression material according to the present invention is a pasty alginate impression material composition comprising a main paste and a setting paste, which is superior in preservability and overcomes the problems of the conventional art so that it is free from change of viscosity and from liquid separation, and does not cause a delay in setting time due to the deterioration. Therefore, the dental alginate impression material according to the present invention is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed is:

1. A composition comprising a main paste and a setting paste, wherein said main paste comprises at least one alginate, water, at least one filler, and from 0.01 to 15% by weight of at least one polysaccharide selected from the group consisting of carrageenan, pullulane, curdlan, xanthane gum, gelian gum, pectin, konjak glucomannan, xyloglucan, guar gum, gum arabic, and locust bean gum, and said setting paste comprises calcium sulfate, a liquid component, and 0.5 to 50% by weight of polybutene.

2. A solid composition obtained by setting the composition of claim 1.

3. The composition of claim 1, wherein the polysaccharide is xanthane gum.

4. The composition of claim 1, wherein the polysaccharides is present in an amount of from 0.1 to 3% by weight.

5. The composition of claim 1, wherein the polybutene has a number average molecular weight of from 300 to 4,000.

6. The composition of claim 1, further comprising one or more additional components selected from the group consisting of an inorganic coloring agent, an organic coloring agent, antiseptic, a disinfectant, a flavor and a perfume.

7. The composition of claim 1, wherein the setting paste further comprises at least one additional component selected from the group consisting of a retarder, a pH regulator, a surfactant and a fluoride.

8. The composition of claim 7, wherein the pH regulator is magnesium oxide or magnesium hydroxide.

9. The composition of claim 1, wherein the main paste comprises 5 wt % of sodium alginate, 8 wt % of diatomaceous earth, 75 wt % of distilled water, and 12 wt % of locust bean gum, and the setting paste comprises 50 wt % of calcium sulfate hemihydrate, 49.5 wt % of liquid paraffin, and 0.5 wt % of polybutene.

10. The composition of claim 1, wherein the main paste comprises 7 wt % of sodium alginate, 20 wt % of diatomaceous earth, 72 wt % of distilled water, and 1 wt % xanthane gum, and the setting paste comprises 50 wt % calcium sulfate hemihydrate, 48 wt % liquid paraffin, and 2 wt % polybutene.

11. The composition of claim 1, wherein the alginate is present in an amount of from about 1 to 10% by weight.

12. The composition of claim 1, wherein the filler is selected from the group consisting of diatomaceous earth, silicic anhydride, talc, calcium carbonate and perlite.

13. The composition of claim 1, wherein the liquid component comprises one or more components selected from the group consisting of a liquid paraffin, an aliphatic alcohol and a fatty acid.

14. The composition of claim 1, wherein the alginate is a water-soluble salt selected from the group consisting of a sodium salt of alginic acid, a potassium salt of alginic acid, an ammonium salt of alginic acid and a triethanolamine salt of alginic acid.

15. The composition of claim 1, wherein the water is ion exchanged water, distilled water or water subjected to sterilization with sodium hypochlorite.

* * * * *